(12) United States Patent
Butler et al.

(10) Patent No.: US 9,974,905 B2
(45) Date of Patent: May 22, 2018

(54) DOSE SETTING MECHANISM FOR A DRUG DELIVERY DEVICE

(75) Inventors: Joseph Butler, Warwickshire (GB); David Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 124 days.

(21) Appl. No.: 13/879,112

(22) PCT Filed: Oct. 11, 2011

(86) PCT No.: PCT/EP2011/067679
§ 371 (c)(1),
(2), (4) Date: Apr. 12, 2013

(87) PCT Pub. No.: WO2012/049142
PCT Pub. Date: Apr. 19, 2012

(65) Prior Publication Data
US 2013/0211377 A1    Aug. 15, 2013

Related U.S. Application Data

(60) Provisional application No. 61/392,754, filed on Oct. 13, 2010.

(30) Foreign Application Priority Data

May 31, 2011    (EP) ..................... 11168192

(51) Int. Cl.
*A61M 5/315*    (2006.01)
*A61M 5/24*    (2006.01)
(Continued)

(52) U.S. Cl.
CPC ...... *A61M 5/31501* (2013.01); *A61M 5/3158* (2013.01); *A61M 5/31525* (2013.01);
(Continued)

(58) Field of Classification Search
CPC ........... A61M 2005/31508; A61M 2005/3151; A61M 2005/3215; A61M 5/24;
(Continued)

(56) References Cited

U.S. PATENT DOCUMENTS 533,575 A     2/1895  Wilkens
4,865,591 A *  9/1989  Sams ................ A61M 5/31553
                                                    222/287

(Continued)

FOREIGN PATENT DOCUMENTS

CN    1606460 A    4/2005
EP    0937471      8/1999
(Continued)

OTHER PUBLICATIONS

Form PCT/IB/326, Notification Concerning Transmittal of International Preliminary Report on Patentability.
(Continued)

*Primary Examiner* — Nathan R Price
*Assistant Examiner* — Weng Lee
(74) *Attorney, Agent, or Firm* — McDonnell Boehnen Hulbert & Berghoff LLP

(57) ABSTRACT

The present invention relates to a dose setting mechanism for a drug delivery device and a method of using same. The mechanism comprises a housing, a mechanism member movable in a first axial direction relative to the housing during dose setting and movable in a second, opposite axial direction relative to the housing during injection, wherein the mechanism member is designed and arranged such that the mechanism member is able to change its condition between a first condition preventing movement in the second axial direction and a second condition allowing movement in the second axial direction, and a switching member forcing the mechanism member to change from its second
(Continued)

condition into its first condition at a predefined position of the movement in the first axial direction during dose setting.

19 Claims, 6 Drawing Sheets

(51) Int. Cl.
*A61M 5/32* (2006.01)
*A61M 5/34* (2006.01)

(52) U.S. Cl.
CPC .... *A61M 5/31535* (2013.01); *A61M 5/31551* (2013.01); *A61M 5/24* (2013.01); *A61M 5/31561* (2013.01); *A61M 5/31563* (2013.01); *A61M 5/31581* (2013.01); *A61M 5/3202* (2013.01); *A61M 5/347* (2013.01); *A61M 5/348* (2013.01); *A61M 2005/3151* (2013.01); *A61M 2005/31508* (2013.01); *A61M 2005/3215* (2013.01)

(58) Field of Classification Search
CPC .......... A61M 5/31501; A61M 5/31525; A61M 5/31535; A61M 5/31551; A61M 5/31561; A61M 5/31563; A61M 5/3158; A61M 5/31581; A61M 5/3202; A61M 5/347; A61M 5/348
USPC .......................................... 604/207–211, 186
See application file for complete search history.

(56) References Cited

U.S. PATENT DOCUMENTS

| 5,104,380 | A | * | 4/1992 | Holman ................. A61M 5/20 604/117 |
| --- | --- | --- | --- | --- |
| 5,226,895 | A | | 7/1993 | Harris |
| 5,279,586 | A | | 1/1994 | Balkwill |
| 5,304,152 | A | | 4/1994 | Sams |
| 5,320,609 | A | | 6/1994 | Haber et al. |
| 5,383,865 | A | | 1/1995 | Michel |
| 5,480,387 | A | | 1/1996 | Gabriel et al. |
| 5,505,704 | A | | 4/1996 | Pawelka et al. |
| 5,582,598 | A | | 12/1996 | Chanoch |
| 5,626,566 | A | | 5/1997 | Petersen et al. |
| 5,674,204 | A | | 10/1997 | Chanoch |
| 5,688,251 | A | | 11/1997 | Chanoch |
| 5,921,966 | A | | 7/1999 | Bendek et al. |
| 5,957,896 | A | | 9/1999 | Bendek et al. |
| 5,961,495 | A | | 10/1999 | Walters et al. |
| 6,004,297 | A | | 12/1999 | Steenfeldt-Jensen et al. |
| 6,193,698 | B1 | | 2/2001 | Kirchhofer et al. |
| 6,221,046 | B1 | | 4/2001 | Burroughs et al. |
| 6,235,004 | B1 | | 5/2001 | Steenfeldt-Jensen et al. |
| 6,248,095 | B1 | | 6/2001 | Giambattista et al. |
| 6,899,698 | B2 | | 5/2005 | Sams |
| 6,936,032 | B1 | | 8/2005 | Bush, Jr. et al. |
| 7,241,278 | B2 | | 7/2007 | Moller |
| 2002/0052578 | A1 | | 5/2002 | Moller |
| 2002/0120235 | A1 | | 8/2002 | Enggaard |
| 2003/0050609 | A1 | | 3/2003 | Sams |
| 2004/0059299 | A1 | | 3/2004 | Moller |
| 2004/0210199 | A1 | | 10/2004 | Atterbury et al. |
| 2004/0267207 | A1 | | 12/2004 | Veasey et al. |
| 2005/0033224 | A1 | | 2/2005 | Kirchhofer et al. |
| 2005/0113765 | A1 | | 5/2005 | Veasey et al. |
| 2006/0153693 | A1 | | 7/2006 | Fiechter et al. |
| 2006/0258989 | A1 | * | 11/2006 | Kirchhofer .................. 604/207 |
| 2009/0275916 | A1 | | 11/2009 | Harms et al. |

FOREIGN PATENT DOCUMENTS

| EP | 0937476 | | 8/1999 |
| --- | --- | --- | --- |
| EP | 1074273 | A1 | 2/2001 |
| WO | 99/38554 | | 8/1999 |
| WO | 01/10484 | | 2/2001 |
| WO | 2004078239 | A1 | 9/2004 |
| WO | 2010063687 | A1 | 6/2010 |
| WO | 2010072662 | A1 | 7/2010 |

OTHER PUBLICATIONS

Office Action issued by the Chinese Patent Office for Chinese Patent Application No. 2014090101194540 dated Sep. 4, 2014.
English Translation of Notice of Reasons for Rejection issued in Japanese Patent Application No. 2013-533172 dated Sep. 1, 2015.

* cited by examiner

Table 1

| Dialled Insulin Dose | Pen Number 1 | Pen Number 2 | Pen Number 3 | Pen Number 4 |
|---|---|---|---|---|
| 2 | Low | Low | Low | Low |
| 4 | Low | Low | Low | Low |
| 6 | Low | Low | Low | Low |
| 8 | Low | Low | Low | Low |
| 10 | Dialable | Low | Low | Low |
| 12 | Dialable | Low | Low | Low |
| 14 | Dialable | Low | Low | Low |
| 16 | Dialable | Low | Low | Low |
| 18 | Dialable | Dialable | Low | Low |
| 20 | Dialable | Dialable | Low | Low |
| 22 | Dialable | Dialable | Low | Low |
| 24 | High | Dialable | Low | Low |
| 26 | High | Dialable | Low | Low |
| 28 | High | Dialable | Low | Low |
| 30 | High | Dialable | Low | Low |
| 32 | High | Dialable | Low | Low |
| 34 | High | Dialable | Low | Low |
| 36 | High | Dialable | Dialable | Low |
| 38 | High | Dialable | Dialable | Low |
| 40 | High | Dialable | Dialable | Low |
| 42 | High | Dialable | Dialable | Low |
| 44 | High | High | Dialable | Low |
| 46 | High | High | Dialable | Low |
| 48 | High | High | Dialable | Low |
| 50 | High | High | Dialable | Low |
| 52 | High | High | Dialable | Low |
| 54 | High | High | Dialable | Low |
| 56 | High | High | Dialable | Low |
| 58 | High | High | Dialable | Dialable |
| 60 | High | High | Dialable | Dialable |
| 62 | High | High | Dialable | Dialable |
| 64 | High | High | High | Dialable |
| 66 | High | High | High | Dialable |
| 68 | High | High | High | Dialable |
| 70 | High | High | High | Dialable |
| 72 | High | High | High | Dialable |
| 74 | High | High | High | Dialable |
| 76 | High | High | High | Dialable |
| 78 | High | High | High | Dialable |
| 80 | High | High | High | Dialable |

Legend:
- Dialable: Dose may be dialled and delivered
- Low: Low Dose - Cannot be dispensed
- High: High dose - Cannot be dialled

FIG. 6

Table 2

| Dialled Insulin Dose | Pen Number 1 | 2 | 3 | 4 |
|---|---|---|---|---|
| 2 | D | D | D | D |
| 4 | H | H | H | H |
| 6 | H | H | H | H |
| 8 | H | H | H | H |
| 10 | D | H | H | H |
| 12 | D | H | H | H |
| 14 | D | H | H | H |
| 16 | D | H | H | H |
| 18 | D | D | H | H |
| 20 | D | D | H | H |
| 22 | D | D | H | H |
| 24 | B | D | H | H |
| 26 | B | D | H | H |
| 28 | B | D | H | H |
| 30 | B | D | H | H |
| 32 | B | D | H | H |
| 34 | B | D | H | H |
| 36 | B | D | D | H |
| 38 | B | D | D | H |
| 40 | B | D | D | H |
| 42 | B | D | D | H |
| 44 | B | B | D | H |
| 46 | B | B | D | H |
| 48 | B | B | D | H |
| 50 | B | B | D | H |
| 52 | B | B | D | H |
| 54 | B | B | D | H |
| 56 | B | B | D | H |
| 58 | B | B | D | D |
| 60 | B | B | D | D |
| 62 | B | B | D | D |
| 64 | B | B | B | D |
| 66 | B | B | B | D |
| 68 | B | B | B | D |
| 70 | B | B | B | D |
| 72 | B | B | B | D |
| 74 | B | B | B | D |
| 76 | B | B | B | D |
| 78 | B | B | B | D |
| 80 | B | B | B | D |

| | |
|---|---|
| D (dotted) | Dose may be dialled and delivered |
| H (hatched) | Low Dose - Cannot be dispensed |
| B (blank) | High dose - Cannot be dialled |

FIG. 7

Table 3

| Dialled Long Acting Insulin Dose | Pen Number | | | | | |
|---|---|---|---|---|---|---|
| | 1 | 2 | 3 | 4 | 5 | 6 |
| | Mix ratio (insulin : GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

| | |
|---|---|
| | GLP-1 Dose - may be dialled and delivered |
| | Low Dose - Cannot be dispensed |
| | High dose - Cannot be dialled |

FIG. 8

DOSE SETTING MECHANISM FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2011/067679 filed Oct. 11, 2011, which claims priority to U.S. Provisional Patent Application No. 61/392,754 filed Oct. 13, 2010 and European Patent Application No. 11168192.0 filed May 31, 2011. The entire disclosure contents of these applications are herewith incorporated by reference into the present application.

FIELD OF INVENTION

The present patent application is generally directed to dose setting mechanisms for drug delivery devices that control minimum and/or maximum possible dose settings and a method of setting and delivering at least a predetermined minimum dose of a medicament. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Such a device is known from WO 2004/078239 A1. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum units that the device can deliver, typically 60 units or 80 units for a manual device, such as a pen-type or syringe injection device.

The drug delivery device of WO 2004/078239 A1 comprises a housing for receiving a dose setting mechanism, a cartridge, a dose dial sleeve with an attached dose dial grip, a clicker, a drive sleeve, a clutch for coupling and decoupling the dose dial sleeve and the drive sleeve, a rotatable piston rod and a button which is pressed for injecting a set dose. The full description of the pen-type injection devices disclosed in WO 2004/078239 A1 is incorporated herein by reference.

To dial a dose a user rotates the dose dial grip. With the clicker and clutch means engaged, the drive sleeve, the clicker, the clutch means and the dose dial sleeve rotate with the dose dial grip relative to the housing and relative to the piston rod. Audible and tactile feedback of the dose being dialed is provided by the clicker and the clutch means. Torque is transmitted through saw teeth between the clicker and the clutch means.

A helical groove on the dose dial sleeve and a helical groove in the drive sleeve have the same lead. This allows the dose dial sleeve to extend from the housing and the drive sleeve to climb the piston rod at the same rate. At the limit of travel, a radial stop on the dose dial sleeve engages a stop provided on the housing to prevent further movement. Rotation of the piston rod is prevented due to the opposing directions of overhauled and driven threads on the piston rod.

Should a user inadvertently dial beyond the desired dosage, the pen-type injector allows the dosage to be dialed down without dispense of medicinal product from the cartridge. The dose dial grip is counter rotated. This causes the system to act in reverse. The torque transmitted through the clutch means causes the saw teeth to ride over one another to create the clicks corresponding to dialed dose reduction. Preferably the saw teeth are so disposed that the circumferential extent of each saw tooth corresponds to a unit dose.

When the desired dose has been dialed, the user may then dispense this dose by depressing the button. This displaces the clutch means axially with respect to the dose dial sleeve causing dog teeth of the clutch means to disengage. However the clutch means remains keyed in rotation to the drive sleeve. The dose dial sleeve and associated dose dial grip are now free to rotate. The axial movement deforms a flexible part of the clicker to ensure the saw teeth cannot be overhauled during dispense. This prevents the drive sleeve from rotating with respect to the housing though it is still free to move axially with respect thereto. This deformation is subsequently used to urge the clicker and the clutch back along the drive sleeve to restore the connection between the clutch and the dose dial sleeve when pressure is removed from the button. The longitudinal axial movement of the drive sleeve causes the threaded piston rod to rotate through a threaded opening in a housing insert, thereby to advance the piston in the cartridge.

In other words, the drive sleeve moves longitudinally, i.e. only in the axial direction, during an injection. Because the drive sleeve and the piston rod are engaged via corresponding threads on the outer surface of the piston rod and an internal face of the drive sleeve, the longitudinal movement of the drive sleeve causes the piston rod to rotate. The housing insert with the threaded opening which is engaged with the piston rod via corresponding threads is fixed within the housing, i.e. prevented from rotation. Thus, the rotating piston rod is screwed through the threaded opening in the housing insert, i.e. the piston rod performs a combined rotational and longitudinal movement along a helical path defined by the corresponding threads of the threaded opening and the piston rod.

Once the dialed dose has been dispensed, the dose dial sleeve is prevented from further rotation by contact of a plurality of members extending from the dose dial grip with a corresponding plurality of stops formed in the housing, thus determining a zero dose position.

Such pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device must also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

SUMMARY

It is an object of the invention to provide a device that reduces or eliminates the risk that a user of an injection device will set and administer a dose below a preselected minimum effective dose of a particular medicament.

This object is solved with a dose setting mechanism as defined in claim 1. One specific means of achieving a minimum settable dose on a variable dose, drug delivery device, such as a pen-type device, is to include a change of state mechanism that prevents dosing of the device until a predetermined minimum dose has been set. A maximum dose mechanism can also be used with a minimum dose mechanism.

The minimum dose limiting function of the present invention is achieved by means of a lock-out component that changes its state, for example, its geometry, and only allows dispensing or delivery of the drug compounds or medicament after a predetermined minimum dose threshold has been reached during dose setting. Alternative methods of utilizing a change of state may include a component that toggles between two or more positions, either translationally, rotationally or both dependent upon the dose dialed, with at least one such position preventing delivery of the dose. Examples of flexible lock-out components include disc-shaped, star-shaped, spoke and hub shaped, cross-shaped, and the like structures.

According to one possible exemplary embodiment of our invention a dose setting mechanism for a drug delivery device is provided comprising a drug delivery device housing, a dose dial sleeve positioned at least partly in the housing and rotatable during dose setting and dose delivery. The mechanism also has a driver directly or indirectly connected to the dose dial sleeve that moves axially during dose setting. There is a lock-out component that is connected to the driver and axially movable during dose setting and dose delivery. Preferably, the housing has a first, second and third housing sections, where the second section has a diameter that is less than the third section. Although the embodiments exemplified herein all show a housing with a reduced diameter, our invention is equally applicable to any section of the housing where there is an interface that defines a change of cross sectional geometry. For example, a change from round to oval or round to square cross sectional geometry could cause the lock-out member to change its state. The lock-out component engages the second housing section during dose setting and disengages the second housing section once a predetermined minimum dose is set. When the set dose is less than a predetermined minimum the lock-out component prevents a user from delivering or injecting the set dose.

Preferably the lock-out component engages a reduced diameter section of the housing when the lock-out component is in a first configuration and disengages the reduced diameter section when the set dose is equal to or greater than a predetermined minimum dose of medicament. Most preferably, the lock-out component comprises a flexible material of construction and the reduced diameter section comprises a plurality of ridges or other friction enhancing features that engage the lock-out component. During dose setting the lock-out component transforms between a first and second configuration. Preferably, the lock-out component is in the second configuration at 0 set dose and is in the first configuration at any set dose greater than a priming dose and less than the minimum allowable dose. During delivery, the lock-out component is in the second configuration when the set dose is equal to or greater than a predetermined minimum.

In one embodiment the reduced diameter section of the housing has an axial length that is proportional to a predetermined minimum settable dose of medicament and the lock-out component is disc-shaped having a convex shape in a first configuration and a concave shape in a second configuration.

The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with the present invention could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of the min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin.

Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (illustrated in FIG. 6) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up would occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2 (illustrated in FIG. 7). Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3 illustrated in FIG. 8, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a mechanism that prevents dosing of the device until a predetermined minimum dose has been reached. A maximum dose mechanism can also be used with a minimum dose mechanism.

The minimum dose limiting function as disclosed herein may be achieved by providing a dose setting mechanism comprising a housing, a mechanism member and a switching member. The mechanism member is movable in a first axial direction relative to the housing during dose setting and movable in a second, opposite axial direction relative to the housing during injection. Further, the mechanism member is designed and arranged such that the mechanism member is able to change its condition or state between a first condition preventing movement in the second axial direction and a second condition allowing movement in the second axial direction. The switching member is designed and arranged such that it forces the mechanism member to change (switch) from its second condition into its first condition at a predefined position of the movement in the first axial direction during dose setting. In other words, the mechanism member prevents a set dose from being delivered if the set dose is less than a predetermined minimum or above a predetermined maximum due to its changing condition and thus allowing or preventing the movement required for dose dispensing.

According to a preferred embodiment the change of condition of the mechanism member involves a change of the geometry of the mechanism member. Thus, the mechanism member may comprise a flexible material of construction allowing to be forced from the second condition into the first condition and to automatically flip back to its second position as soon as the switching member releases or disengages the mechanism member.

More specifically, the mechanism member preferably comprises a flexible disc or a flexible finger bent in a first curvature in its unstressed condition, wherein the flexible disc or flexible finger is allowed to elastically flip its orientation under a load exerted by the switching member and to flip back to its original state in its unstressed condition. In other words, the mechanism member (lock-out component) is e.g. disc-shaped and convex in a first configuration and concave in a second configuration.

Although it is preferred if the mechanism member is allowed to change into its second condition as soon as any external load is released, the present invention also includes embodiments where the mechanism member remains in its first condition and only switches back to the second condition upon contact by a further switching member.

In general terms, the switching member may comprise a protrusion engaging the mechanism member during its movement in the first axial direction during dose setting this causing the mechanism member to change its condition. Preferably, the housing comprises at least one first section having a first diameter, and at least one second section having a second, smaller diameter with this second smaller diameter section forming the switching member. As an alternative to a housing section having a smaller diameter, an insert, e.g. a sleeve, may be provided reducing the diameter of the housing.

Irrespective of the aforementioned features, a dose setting mechanism according to the present invention may comprise a drug delivery device housing, a dose dial sleeve positioned at least partly in the housing and rotatable during dose setting and dose delivery, a driver releasably connected to a dose dial sleeve, where the driver moves axially during dose setting and a lock-out component (mechanism member) connected to the driver and being axially movable during dose setting and dose delivery. The housing preferably has first, second and third housing sections, where the second section has a change of cross sectional geometry at an interface with the third housing section. Thus, the second housing section may form a switching member. The mechanism member (lock-out component) engages the second housing section in a locking configuration during dose setting. Further, the lock-out component disengages the second housing section when at least a predetermined minimum dose is set. In other words, the lock-out component is engaged with the housing when the lock-out component is in a first configuration and disengaged from the housing when a predetermined minimum dose of medicament has been set. To increase the reliability and the resistance preventing movement in one direction in the first state of the mechanism member, the mechanism may comprise a plurality of ridges that engage the lock-out component.

To prevent a user from dispensing a dose which is below a predefined minimum value, the mechanism member and the switching member are arranged such that the mechanism member is forced in its first condition during a first part of its axial movement and is released to switch into its second condition at a predefined position of its axial movement during dose setting corresponding to a minimum dose. Further, to prevent a user from dispensing a dose which is above a predefined maximum value, the mechanism member and the switching member are arranged such that the mechanism member is forced from its second condition into its first condition at a predefined position of its axial movement during dose setting corresponding to a maximum dose. The minimum dose and/or maximum dose thresholds may be preset by a health care provider according to the individual requirements of a patient or may be fixed during assembly of the device.

According to a preferred embodiment, the dose setting mechanism further comprises a driver and/or a dose setting member, wherein at least one of the driver and the dose setting member is movable in the first axial direction relative to the housing during dose setting and is movable in the second, opposite axial direction relative to the housing during injection. If the mechanism member is associated to or fixed to the driver or dose setting member to follow its axial movement, this provides for the required movement of the mechanism member during use of the device. The driver may be releasably connected to the dose dial sleeve and the driver moves axially while rotating during dose setting. The mechanism member (lock-out component) may be connected to the driver and is axially and rotationally movable during dose setting.

The amount of the preselected minimum dose or maximum dose may not only be defined by the position of the switching member but also by its size. In other words, the switching member extends over a predefined length in the axial direction for holding the mechanism member in its first condition.

The mechanism member (lock-out component) may be in the second configuration at 0 set dose and may be in the first configuration at any set dose greater than a priming dose and less than a predetermined minimum dose during dose setting. Further, the mechanism member (lock-out component) may be in the second configuration at any set dose equal to or greater than a predetermined minimum dose.

Irrespective of the aforementioned features, a dose setting mechanism according to the present invention may comprise a drug delivery device housing having a first cross sectional geometry that is different than a second cross sectional geometry; a dose dial sleeve positioned in the housing and rotatable during dose setting and dose delivery; a driver connected to the dose dial sleeve that moves axially during dose setting; and a flexible lock-out component (mechanism member) connected to the driver and axially movable during dose setting and dose delivery, where the driver is locked axially when the lock-out component is engaged with the first cross sectional geometry of the housing. Further, it is preferred if the first cross sectional geometry of the housing has an axial length that is proportional to a predetermined minimum settable dose of medicament. In addition, dose delivery may be prohibited when the lock-out component is within the first cross sectional geometry of the housing if a predetermined minimum settable dose of medicament has not been set.

As mentioned above, the first and second cross sectional geometries of the housing may be part of an insert attached to the housing. This insert can be fixed into position at the assembly stage of the dose setting mechanism using snap features, adhesives, plastic welding techniques or similar methods. This offers the advantage that the body can remain standard (e.g., uniform in diameter) while various lengths of reduced diameter section inserts are used to control and set the predetermined minimum dose quantity. Such inserts would be added during device manufacture. Alternatively, a health care provider may add these inserts to the device post manufacture to change the predetermined minimum dose.

The following is a method of delivering at least a predetermined minimum dose of a medicament according to the present invention comprising: setting a dose by rotating a dose dial sleeve in a first direction relative to a device housing, where the sleeve is in clutched engagement with a driver causing the driver and sleeve to move in a proximal axial direction; transforming a mechanism member (lock-out component) attached to the driver from a second configuration to a first configuration as the driver moves proximally during dose setting; transforming the lock-out component to the second configuration once the set dose equals or is greater than a predetermined minimum dose; and preventing rotation of the dose dial sleeve in a second direction opposite the first direction when a dose of from 0 to less than a predetermined minimum dose is set.

Further, during setting the dose by rotating the dose dial sleeve in the first direction relative to the device housing, the sleeve is in clutched engagement with the driver causing the driver and sleeve to move in a proximal axial direction while rotating.

A user can according to one embodiment manually override the minimum dose function if required by dialing a dose equal to, or greater than, the predetermined minimum dose and then dialing back down to the required dose level. Additionally, the dose count numbers below the minimum dose may be colored a different color such as red to differentiate that the dose dialed is less than the normal minimum dose. By altering the distance between the "zero dose position" and the start of the reduced diameter section a second permissible dose window is permitted. This second dose window starts at 0 units dialed and ends at the point where the lock-out component enters the reduced diameter section and flips into its downwards biased condition.

The second dose window can therefore be designed to enable the user to dispense "air shots" or "priming doses" that would otherwise be below the minimum dose threshold.

Alternatively, the "air shot" or "priming dose" function can be provided by designing the lock-out component to only transform after a certain number of units have been dialed. In one embodiment where the lock-out component is a flexible disc, when the dose setting mechanism is in the zero dose position the flexible disc is in its un-deformed or upwards biased condition with the edges of the disc about to enter the reduced diameter section. As the user dials a dose, the center of the disc moves upwards and the restrained edges of the disc will start to deform elastically. After a pre-defined dose has been dialed, the edges of the disc will be deformed to the same diameter as the reduced diameter section and will therefore move into this section in the downwards-biased (locking) condition. Prior to this predefined dose the disc edges will not have entered the reduced diameter section and it is therefore possible to dial and dispense doses below this pre-defined dose without the flexible disc causing the mechanism to lock.

These as well as other advantages of various aspects of our proposed drug delivery device will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 6 illustrates Table 1 showing dialed insulin doses for an example family of delivery devices;

FIG. 7 illustrates Table 2 showing dialed insulin doses for an example family of delivery devices; and FIG. 8 illustrates Table 3 showing dialed insulin doses for an example family of pen-type injection devices.

DETAILED DESCRIPTION

Figure 1:
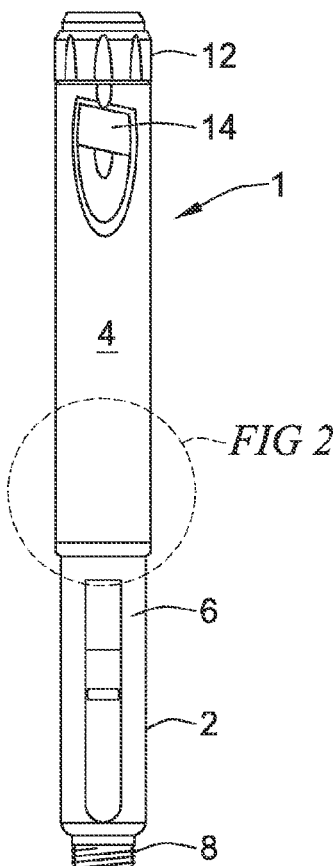
FIG. 1 illustrates a generic design of a pen-type drug delivery device capable of accepting the min/max functionality of the invention.

Referring to FIG. 1, there is shown a drug delivery device 1 in accordance with an exemplary pen-type design arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge retaining part 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6. Preferably, a cartridge (not shown) from which a number of doses of a medicinal product may be dispensed, is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver engaged with a spindle (not illustrated in FIG. 1, but are illustrated as items 5 and 3, respectively, in FIG. 2). The driver 5 is preferably threadedly engaged to a spindle or piston rod 3. Also part of the drive mechanism, which generally includes the dose dial sleeve, driver, piston rod, is a clutch or other release mechanism (not shown) that directly or indirectly, releasably couples the dose dial sleeve 20 to the driver 5. Preferably, the driver is coupled to the dose dial sleeve during dose setting and uncoupled during dose delivery.

The cartridge housing 6 has a distal end and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

Figure 2:
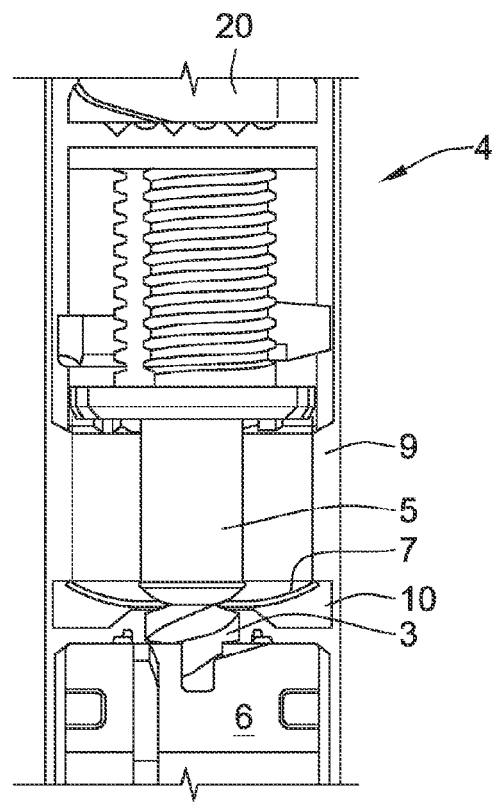
FIG. 2 illustrates a sectional view of a drug delivery device showing one possible embodiment of the dose setting mechanism of the invention.

FIG. 2 illustrates a cut-away and enlarged section of the dose setting mechanism 4 having a driver 5 and dose dial sleeve 20. In this one embodiment the lock-out component (mechanism member) is a flexible disc element 7 that is attached or otherwise fixed to driver 5 of the dose setting mechanism. The flexible disc element 7 is normally biased upwards (concave) in a proximal direction as shown in FIG. 2. The body of the device incorporates a reduced diameter section 9 that interferes with the flexible disc element 7 causing elastic deformation of the flexible disc element 7 to a first configuration or concave shape as it travels from one diameter 10 past the reduced diameter section 9. The extremities of the flexible disc element 7 are deformed distally during dose setting, and deformed proximally when a dose is delivered. In other words, initially the lock-out component 7 is in a second or concave position at zero dose in diameter section 10, then as the dose is being set and the driver 5 is moving proximally, the lock-out component moves into the section of the housing with reduced diameter 9 causing the extremities of the lock-out component to invert changing the shape to a first or convex position. After moving out of the reduced diameter section when the predetermined minimum dose is exceeded, the lock-out component transforms again back to the second or concave configuration. When the lock-out component is in the first configuration in the reduced diameter section of the housing the injection device is locked and a user will be prevented from delivering a set dose less than the predetermined minimum. However, when the lock-out component is in the concave position when in the upper or proximal section, where the diameter is larger, the lock-out does not lock the device.

Figure 3:
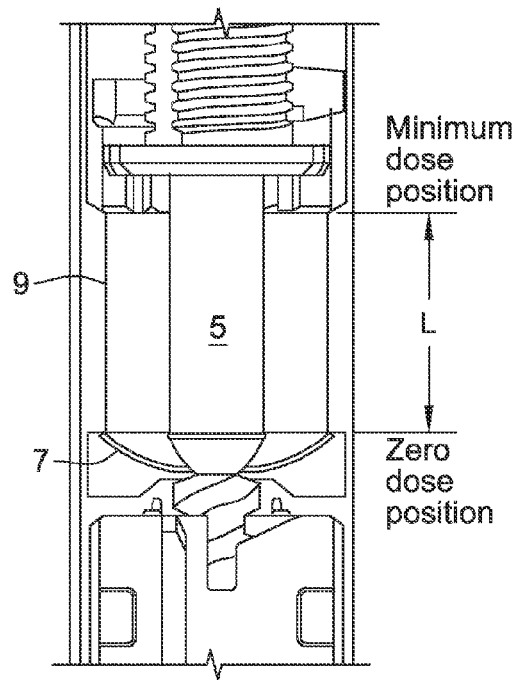
FIG. 3 illustrates a close-up sectional view of the embodiment of the dose setting mechanism shown in FIG. 2.

The length and position of the reduced diameter section 9 controls the minimum dose value that must be set before it is possible to deliver a dose. This is illustrated in FIG. 3 where the flexible disc element 7 is at a no dose or zero dose dialed state. As a dose is dialed the flexible disc element 7 enters section 9 and changes its state by elastically flipping its orientation and then travels axially for length L until the minimum dose has been dialed, at which point the flexible disc element 7 leaves the reduced diameter section 9 and returns to its free proximally biased concave geometric shape. L can be adjusted to change the minimum predetermined dose.

Figure 4:
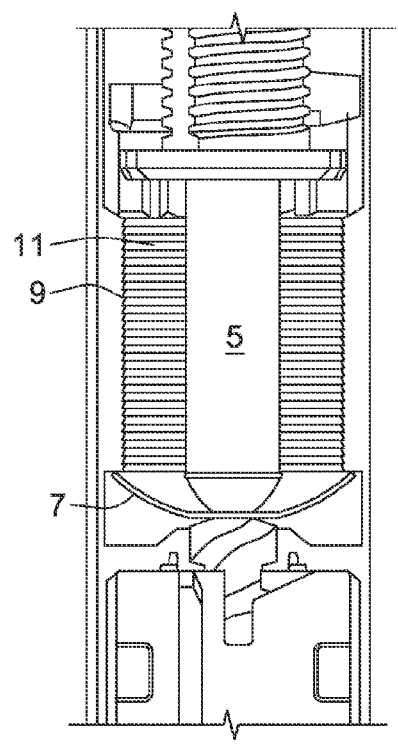
FIG. 4 illustrates a sectional view of another possible embodiment of the dose setting mechanism of the invention.

Before the minimum dose has been dialed, if a user attempts to deliver a dose the flexible disc element 7 locks against the reduced diameter section 9 wall, for example by friction as the flexible elements "bite" into the wall. This locking prevents axial movement of the drive mechanism, thereby preventing dose delivery and offering immediate feedback to the user. The geometry and material of the lock-out component 7 ensure that there is minimal friction during normal dose delivery operation and during setting of a dose. To further increase the locking strength of the lock-out component 7 against the reduced diameter section 9, the inner surface of the reduced diameter section may incorporate friction enhancing features, such as the ratchet style ridges or protrusions 11 shown in FIG. 4. Although the geometry of the flexible disc element 7 in the Figures is shown as a 4-way petal arrangement, any shape or material construction may be used provided the lock-out component prevents the user from delivering a set dose when the lock-out component is in the reduced diameter section 9 of the housing. Most preferably, the lock-out component has a number of flexible fingers or slots to optimize deformation and locking strength.

Figure 5:
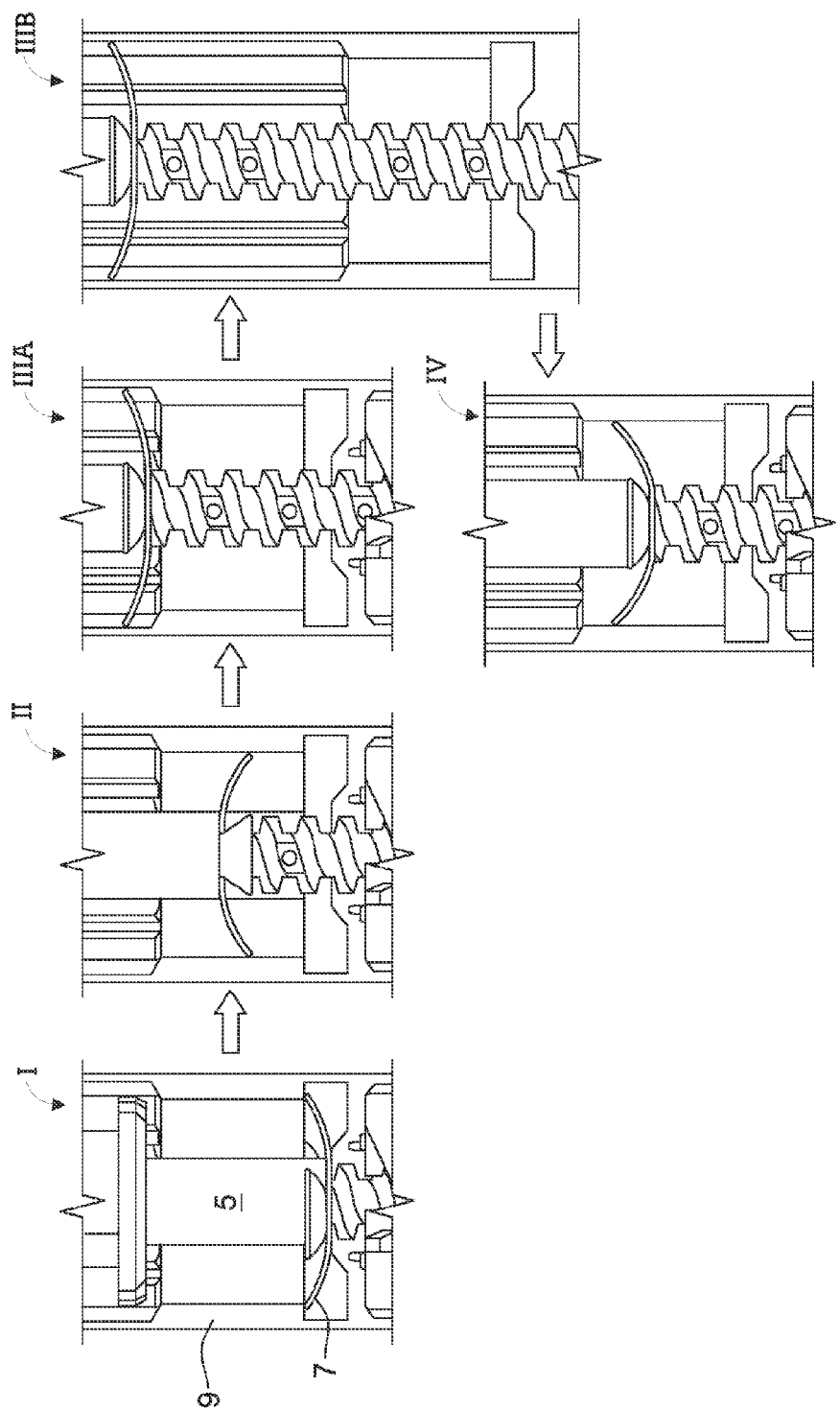
FIG. 5 illustrates the operation the drug delivery device of FIG. 2 in a cross sectional view.

With reference to FIG. 5, the specific operating principle of the flexible disc 7 of this one possible embodiment of our invention is as follows:

I. Initial position: Flexible disc 7 is biased upwards in a proximal direction and is below the reduced diameter section 9 of the device housing.

II. A dose less than the minimum user dose has been dialed. The flexible disc 7 has changed shape as it entered the reduced diameter section 9. If the user attempted to deliver a dose (i.e., by moving the driver in a distal direction), the flexible disc locks onto the reduced diameter section thereby preventing movement of the driver and thus delivery of the set dose of medicament.

IIIa. The minimum user dose has been dialed. The flexible disc is clear of or axially past the reduced diameter section and therefore returns or transforms back to its original free concave shape.

IIIb. The user continues to dial to a correct dose. The driver 5 and flexible disc 7 travel in a proximal direction as the dialed dose is increased.

IV. As the dose is delivered, the flexible disc deforms, but is not transformed, and travels into the reduced diameter section with minimal drag or friction. Once the dose is fully delivered, the flexible disc returns to its free or relaxed position ready for the next dose operation.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the present invention.

For the purposes of the present invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

Exemplary embodiments of the present drug delivery device have been described. Those skilled in the art will understand, however, that changes and modifications may be made to these embodiments without departing from the true scope and spirit of the presently proposed drug delivery device, which is defined by the claims.

The invention claimed is:

1. Dose setting mechanism for a drug delivery device, the dose setting mechanism comprising:
   a housing;
   a disc or finger movable in a first longitudinal axial direction relative to the housing during dose setting and movable in a second, opposite longitudinal axial direction relative to the housing during injection,
   wherein the disc or finger is designed and arranged such that the disc or finger is able to change its condition between a first condition preventing longitudinal axial movement in the second longitudinal axial direction and a second condition allowing longitudinal axial movement in the second longitudinal axial direction; and
   a protrusion forcing the disc or finger to change from its second condition into its first condition at a predefined position of the longitudinal axial movement of the disc or finger in the first longitudinal axial direction during dose setting
   wherein in the first condition, the longitudinal axial movement of the disc or finger in the second axial direction is prevented, and
   in the second condition, the longitudinal axial movement of the disc or finger in the second longitudinal axial direction is allowed,
   wherein the disc or finger comprises a flexible disc or a flexible finger bent in a first curvature in its unstressed condition, wherein the flexible disc or flexible finger is allowed to elastically flip its orientation under a load exerted by the protrusion.

2. Dose setting mechanism according to claim 1, wherein the change of condition of the disc or finger involves a change of the geometry of the disc or finger.

3. Dose setting mechanism according to claim 1, wherein the protrusion engages the disc or finger during its longitudinal axial movement in the first longitudinal axial direction during dose setting this causing the disc or finger to change its condition.

4. Dose setting mechanism according to claim 1, wherein the housing comprises at least one first section having a first diameter, and at least one second section having a second, smaller diameter forming the protrusion.

5. Dose setting mechanism according to claim 1, wherein the disc or finger and the protrusion are arranged such that the disc or finger is forced in its first condition during a first part of its longitudinal axial movement and is released to switch into its second condition at a predefined position of its longitudinal axial movement during dose setting corresponding to a minimum dose.

6. Dose setting mechanism according to claim 1, wherein the disc or finger and the protrusion are arranged such that the disc or finger is forced from its second condition into its first condition at a predefined position of its longitudinal axial movement during dose setting corresponding to a maximum dose.

7. Dose setting mechanism according to claim 1 further comprising a driver and/or a dose setting member movable in the first longitudinal axial direction relative to the housing during dose setting and movable in the second, opposite longitudinal axial direction relative to the housing during injection, wherein the disc or finger is associated to or fixed to the driver or dose setting member to follow its longitudinal axial movement.

8. Dose setting mechanism according to claim 1, wherein the protrusion extends over a predefined length in the axial direction for holding the disc or finger in its first condition.

9. Dose setting mechanism according to claim 1, wherein the housing has first, second and third housing sections, where the second section has a change of cross sectional geometry at an interface with the third housing section.

10. Dose setting mechanism according to claim 9, wherein the disc or finger engages the second housing section in a locking configuration during dose setting, and wherein the disc or finger disengages the second housing section when at least a predetermined minimum dose is set, thus preventing a set dose from being delivered if the set dose is less than a predetermined minimum.

11. Dose setting mechanism according to claim 9, wherein the change of cross sectional geometry of the second housing section comprises a plurality of ridges that engage the disc or finger.

12. Dose setting mechanism according to claim 9, wherein the disc or finger is in a second configuration at 0 set dose and is in a first configuration at any set dose greater than a priming dose and less than a predetermined minimum dose during dose setting.

13. Dose setting mechanism comprising,
a housing;
a disc or finger movable in a first longitudinal axial direction relative to the housing during dose setting and movable in a second, opposite longitudinal axial direction relative to the housing during injection,
wherein the disc or finger is designed and arranged such that the disc or finger is able to change its condition between a first condition preventing longitudinal axial movement in the second longitudinal axial direction and a second condition allowing longitudinal axial movement in the second longitudinal axial direction; and
a protrusion forcing the disc or finger to change from its second condition into its first condition at a predefined position of the longitudinal axial movement of the disc or finger in the first longitudinal axial direction during dose setting
wherein in the first condition, the longitudinal axial movement of the disc or finger in the second axial direction is prevented, and
in the second condition, the longitudinal axial movement of the disc or finger in the second longitudinal axial direction is allowed
said dose setting mechanism further comprising:
a drug delivery device housing having a first cross sectional geometry that is different than a second cross sectional geometry;
a dose dial sleeve positioned in the housing and rotatable during dose setting and dose delivery,
a driver connected to the dose dial sleeve that moves longitudinal axially during dose setting; and
a flexible lock-out component connected to the driver and longitudinal axially movable during dose setting and dose delivery, wherein the flexible lock-out component comprises the disc or finger,
wherein the driver is locked longitudinal axially when the lock-out component is engaged with the first cross sectional geometry of the housing.

14. Dose setting mechanism for a drug delivery device, the dose setting mechanism comprising:
a housing;
a flexible disc movable in a first longitudinal axial direction relative to the housing during dose setting and movable in a second, opposite longitudinal axial direction relative to the housing during injection,
wherein the flexible disc is designed and arranged such that the flexible disc is able to change its condition between a first condition preventing longitudinal axial movement in the second axial direction and a second condition allowing longitudinal axial movement in the second axial direction; and
a protrusion forcing the flexible disc to change from its second condition into its first condition at a predefined position of the longitudinal axial movement of the flexible disc in the first axial direction during dose setting.

15. Dose setting mechanism for a drug delivery device, the mechanism comprising:
a housing;
a mechanism member movable in a first longitudinal axial direction relative to the housing during dose setting and movable in a second, opposite longitudinal axial direction relative to the housing during injection,
wherein the mechanism member is designed and arranged such that the mechanism member is able to change its condition between a first condition preventing longitudinal axial movement in the second longitudinal axial direction and a second condition allowing longitudinal axial movement in the second longitudinal axial direction; and
a switching member forcing the mechanism member to change from its second condition into its first condition at a predefined position of the longitudinal axial movement of the mechanism member in the first longitudinal axial direction during dose setting wherein in the first condition, the longitudinal axial movement of the mechanism member in the second axial direction is prevented, and
in the second condition, the longitudinal axial movement of the mechanism member in the second longitudinal axial direction is allowed.

16. Dose setting mechanism according to claim 15, wherein the change of condition of the mechanism member involves a change of the geometry of the mechanism member.

17. Dose setting mechanism according to claim 15, wherein the switching member comprises a protrusion to engage the mechanism member during its longitudinal axial movement in the first longitudinal axial direction during dose setting this causing the mechanism member to change its condition.

18. Dose setting mechanism according to claim 15, wherein the mechanism member and the switching member are arranged such that the mechanism member is forced in its first condition during a first part of its longitudinal axial movement and is released to switch into its second condition at a predefined position of its longitudinal axial movement during dose setting corresponding to a minimum dose.

19. Dose setting mechanism according to claim 15, wherein the mechanism member and the switching member are arranged such that the mechanism member is forced from its second condition into its first condition at a predefined position of its longitudinal axial movement during dose setting corresponding to a maximum dose.

* * * * *